United States Patent
Ferreira et al.

(10) Patent No.: US 6,790,668 B1
(45) Date of Patent: Sep. 14, 2004

(54) MONITORING PATIENT COMPLIANCE AND BIOAVAILABILITY OF DRUGS BY DEPROTEINIZING BODY FLUIDS

(75) Inventors: Milton F. Ferreira, Rio de Janeiro (BR); Vera L. Luiza, Rio de Janeiro (BR); Eduardo W. Barroso, Rio de Janeiro (BR); André L. Gemal, Rio de Janeiro (BR)

(73) Assignee: Fundacao Oswaldo Cruz - Fiocruz, Rio de Janeiro (BR)

( * ) Notice: Subject to any disclaimer, the term of this patent is extended or adjusted under 35 U.S.C. 154(b) by 0 days.

(21) Appl. No.: 09/600,594

(22) PCT Filed: Nov. 23, 1999

(86) PCT No.: PCT/BR99/00096

§ 371 (c)(1),
(2), (4) Date: Sep. 7, 2000

(87) PCT Pub. No.: WO00/31531

PCT Pub. Date: Jun. 2, 2000

(30) Foreign Application Priority Data

Nov. 23, 1998 (BR) ............................................. 9804648

(51) Int. Cl.⁷ ................................................. G01N 1/34
(52) U.S. Cl. ............................ 436/161; 436/92; 436/93; 436/96; 436/98; 436/164; 436/175; 436/177
(58) Field of Search ................................. 436/175, 177, 436/91, 92, 93, 96, 98, 161, 164; 422/61, 70, 72

(56) References Cited

U.S. PATENT DOCUMENTS

| | | | |
|---|---|---|---|
| 4,656,141 A | 4/1987 | Birks et al. | |
| 5,135,875 A | 8/1992 | Meucci et al. | |
| 5,198,541 A | * 3/1993 | Elsbach et al. | |
| 6,333,061 B1 | * 12/2001 | Vadhar | |

FOREIGN PATENT DOCUMENTS

| EP | 471295 A1 | 2/1992 |
|---|---|---|
| EP | 0 122 032 | 10/1998 |

OTHER PUBLICATIONS

Chemical Abstract No. 1992:15243. Bergqvist et al., J. Chromatogr. (1991), 571 (1–2), 169–77.*

Chemical Abstract No. 1990:30169. Lam et al., J. Liq. Chromatogr. (1989), 12(10), 1851–72.*

Zhang, W. et al. "Study on HPLC assay for the plasma concentration of rifampicin and its pharmacokineics of microsphere formulation". Zhongguo Kangshengsu Zazhi 1996, 21 (4), 273–276 (CH), Columbus, Ohio, USA, Chem. abstract, vol. 126, No. 8, Feb. 1997, p. 1052, column 1, abstract No. 109002y.

* cited by examiner

*Primary Examiner*—Jan M. Ludlow
(74) *Attorney, Agent, or Firm*—Nixon & Vanderhye P.C.

(57) ABSTRACT

The present invention is a method for drug level detection by using a simplified and effective deproteinizing step from body fluids, such as plasma, blood, urine, saliva, tear fluid, followed by drug extraction and measurement using an accurate technique, such as a colorimetric assay or a High-Performance Liquid Chromatography method. In a particular embodiment, the invention is directed to a method to quantify rifampicin in order to monitor its levels in body fluids and also to a Kit for rifampicin concentration measurement.

18 Claims, 5 Drawing Sheets

MONITORING PATIENT COMPLIANCE AND BIOAVAILABILITY OF DRUGS BY DEPROTEINIZING BODY FLUIDS

This application is the national phase of international application PCT/BR99/00096 filed Nov. 23, 1999 which designated the U.S.

The present invention relates to methods of determining the concentration of a selected drug in the body of a subject to provide the monitoring of either drug levels in a clinical setting and in public health services and patient compliance with medication prescriptions. The methods are characterized by a simplified and effective deproteinizing body fluid step followed by drug extraction and measurement using an accurate technique, such as a colorimetric assay or a High-Performance Liquid Chromatography method.

BACKGROUND OF THE INVENTION

In the field of medicine, a number of medications have been found safe and efficacious for the treatment of patients with physical illnesses. Patients placed on prescribed medication treatment plans are typically monitored. Subjective and objective methods are used to identity bothersome symptoms and to implement any changes necessary during the course of treatment. Monitoring may continue for as long as treatment is provided.

Currently, the most common method of monitoring patients for medication compliance is clinical observation which involves individual counseling and close personal supervision by physicians which observe physiological signs and symptoms or residual signs of illness and also listen to patient complaints regarding degree of pain relief and evaluate physiological changes over time. This method is time consuming, expensive and highly subjective. Needless to say, it is fraught with potential errors.

Additional compliance information can also be obtained using qualitative urine monitoring methods such as the standard laboratory procedure called enzyme-multiplied immunoassay (EMIT). Utilizing an arbitrary cutoff value, these methods provide the clinician with a simple positive or negative indication of the possible presence or absence of a parent drug or its metabolites in a patient's urine. The parent drug is the prescribed medication itself and the metabolites are those chemical derivatives of the medication which naturally occur upon the patient's body metabolizing the medication. These tests do not provide information concerning the time or amount of last drug use or whether or not the prescribed dose of medication was ingested properly, diverted or supplemented.

Physicians utilizing only clinical evaluation and qualitative urine drug screening test results may develop problems in their treatment methods. Consistently, Fox, W. (Fox, W. (1990). "Drug combinations and bioavailability of rifampicin". Tubercle. 71: 241–5) suggested parallel serum/plasma sampling in selected studies for testing abroad to verify the tuberculosis treatment effectiveness using drug combinations by confirming the urinary bioavailability determination. In the mentioned text, the term "abroad" means outside developing countries in which expensive analytical equipment is not commonly found.

Another monitoring method sometimes used is a direct measurement of parent drug concentrations or active metabolites concentrations of the drug in plasma and other body fluids. This direct method presents some limitations since it is expensive and requires the use of time consuming and highly technical analytical procedures such as high-performance liquid chromatography and mass spectrometry since active and inactive metabolites must be quantified separately.

Attempts have been made to overcome the difficulties of the sophisticated analytical procedures. In the EP 122 032, it is described a method of determining the concentration of a selected drug in the body of a subject consisting of the steps of holding a liquid collecting means comprising an absorbent inert member, containing a reagent substance which reacts with selected drug, in a position in close proximity to an eye of the patient for collecting tear fluid therefrom and allowing the tear fluid collected to come into contact with said reagent substance during a period sufficient to permit the development of the reaction which has to be physically detectable. It is mentioned that this method provides a readily indication of she level of said drug in the body because the tear fluid is less complex then other body fluids such as blood. Nevertheless, this assay permits only qualitative or semi-quantitative drug detection.

Although simplicity is an important quality when dealing with monitoring methods, the accuracy of the assay is crucial in the control of diseases, e.g. tuberculosis, specially to measure small quantities of drugs in complex body fluids, such as blood. In the U.S. Pat. No. 4,656,141 it is proposed a high-performance liquid chromatography process for detecting the presence of trace amounts of non-fluorescent soluble compounds each having at least one labile hydrogen atom in a carrier solution by adding a non-fluorescent quinone which is reducible to a fluorescent hydroquinone, and irradiating the resulting solution in the absence of oxygen with light of sufficient energy to cause the quinone to be reduced to a hydroquinone.

Preferably both quantitative and analytical methods should be used to follow the patient on a repetitive basis to ensure that the patient is indeed ingesting the prescribed amounts of medication in the proper manner and responding as expected. Moreover, in control programmes of Public Health Services, confident monitoring of treatment is crucial. Tuberculosis Control Program may be cited as a representative example of this approach and Rifampicin as a highly potent drug widely used for tuberculosis treatment.

An efficient follow up the other drugs treatment performance is also important. Examples are anti-retroviral drugs, such as proteinase or reverse transcriptase inhibitors, e.g. 2',3'-dideoxyinosine (ddI), 2',3'-dideoxycytidine (ddC) or 3'-azido-2,3'-dideoxythymidine (AZT) (see Frijus-Plessen N., Michaelis H. C., Forth H. e Kahl G. F. (1990). "Determination of 3'-azido-3'-deoxythymidine, 2',3'-dideoxycytidine, 3'-fluoro-3'-deoxythymidine and 2',3'-dideoxyinosine in biological samples by high-performance liquid chromatography". Chrombio. Elsevier Science Publishers B. V. Amsterdam. 534: 101–107), anti-fungal drugs, e.g. itraconazole which is also used in anti-leishmanial chemotherapy. (Anon: British Society for Antimicrobial Chemotherapy Working Party: Laboratory monitoring of antifungal chemotherapy. The Lancet. Vol. 337. pp. 1577–1580. 1991) or antimonials, the most used anti-leishmanial drug (World Health Organization. Tropical Disease Research. Twelfth Programme Report. World Health Organization Geneva, Switzerland. Pp 139.1995).

In the case of patients with tuberculosis, there has been increasing interest in the determination of serum levels of the main antituberculosis drugs, in particular the most used rifampicin medication. The usual methods for rifampicin assay are colorimetry, microbiology and high-performance liquid chromatography. In the beginning, microbiological assays were employed by using *Sarcina lutea* or *Staphylococcus aureus*. Examples are described in: Furesz S., Scotti, P., Pallanza R., Mapelli E. (1967). "Rifampicin: A new, rifampicin. III Absorption, distribution and elimination in man". Arzneim-Forsch. 17: 534–7; Boman, G. (1974). "Serum concentration and half-life of rifampicin after simultaneous oral administration of aminosalicylic acid or isoniazid". Europ J Clin Pharmacol. 7: 217–25; Dickinson, J. M., Aber, V. R., Allen, B. W., Ellard, A., Mitchison, D. A. (1974). "Assay of rifampicin in serum". J Clin Path. 27: 457–62; Buniva, G., Pagani, V., Carozzi, A. (1983). "Bioavailability of rifampicin capsules". Int J Clin Pharmacol Therapy Toxicol. 21: 404–9; Immanuel, C., Jayasankar, K., Narayana, A. S. L., Saema, G. R. (1985). "Self-induction of rifampicin metabolism in man". Indian Med Res. 82: 381–7. However, the precision of such methods is generally poorer than would be expected with HPLC methods.

Colorimetric methods are interesting under the point of view of easier accomplishing. The procedures or such methods are described in: Maggi, N., Furesz, S., Pallanza, R., Pelizza G. (1969). "Rifampicin desacetylation in the human organism". Arzneim-Forsch. 19: 651–4; Sunahara, S. , Nakagawa, H. (1972). "Metabolic study and controlled clinical trials of rifampicin". Chest. 61: 526–32; Jeanes, C. W. L., Jessamine, A. G., Eidus, L. (1972). "Treatment of chronic drug-resistant pulmonary tuberculosis with rifampicin and ethambutol". Canad Med Ass J. 106: 884–8; Brechbuhler, S., Flueher, H., Riess, W. (1978). "The renal elimination of rifampicin as a function of the oral dose". Arzneim-Forsch. 26: 480–3; McConnell, J. B., Smith, H., Davis, M., Williams, R. (1979). "Plasma rifampicin assay for an improved solvent extraction technique". Br J Clin Pharmc. 8: 506–7; Israili, Z. H., Rogers C. M., El-Attar, H. (1987). "Pharmacokinetics of antituberculosis drugs in patients". J Clin Pharmacol. 27: 78–83

High-Performance Liquid Chromatography (HPLC) has been used for separate determination of rifampicin and its metabolites. HPLC procedures are described in: Goucher, C. R., Peters, J. H., Gordon, G. R., Murray, J. F., Ichikawa, W., Welch, T. M., Gelber, R. H. (1977) "Chemical and bacteriological assays of rifampicin, rifampicin-quinone and desacetylrifampicin". 12th U.S.-Japan Joint Conference on Leprosy. Boston. Mass. Sep. 27–29, 1977. pp. 47–59; Lecaillon, J. B., Febvre, N., Metayer, J. P., Souppart, C. (1978). "Quantitative assay or rifampicin and three of its metabolites in human plasma, urine and saliva by high-performance liquid chromatography". J Chromatogr. 145: 319–24; Ratti, B., Kosina-Parenti, R., Toseili A., Zerrili, L. F. (1981). "Quantitative assay of rifampicin and its metabolite 25 desacetyl-rifampicin in human plasma by reversed-phase high-performance liquid chromatography". J Chromatogr. 225: 526–31; Guillaumant, M., Leclercq, M., Forbert, Y., Guise, B., Harf, R. (1982). "Determination of rifampicin, desacetylrifampicin, isoniazid and acetylisoniazid by high performance liquid chromatography: Application to human serum extracts, polymorphonucieocytes and alveolar macrophages". J Chromatogr. 232: 369–76; Acocella, G., Nonis, A., Gialdroni-Grassi, G., Grassi, C. (1988). "Comparative bioavailability of isoniazid, rifampicin, and pyrazinamide administered in free combination and in a fixed triple formulation designed for daily use in antituberculosis chemotherapy". Am Rev Respir Dis. 138: 882–5; Ishii, M., Agata, H. (1988) "Determination of rifampicin and its main metabolites in human plasma". J Chromatogr. 426: 412–6; Nau, R., Prange, W. H., Menck, S., Kolenda, H., Visser, K., Seydel, J. K. (1992). "Penetration of rifampicin into the cerebrospinal fluid of adults with uninflamed meninges". J Antimicrob Chemother. 29: 719–24; Chouchane, N., Barre, J., Toumi, A., Tillement, J. P., Benakis, A. (1995). "Bioequivalence study of two pharmaceutical forms of rifampicin capsules in man". Eur J Drug Metab Pharmacokin. 20: 315–20.

While providing useful information relative to patient status and treatment compliance, the clinical monitoring methods described above, i. e. clinical interviews with patients, direct plasma drug measurement and qualitative urine drug screening, have distinct drawbacks which limit their usefulness in extended treatment programmes. Although being effective, the complex assays with many extraction steps, e.g. HPLC, require expensive equipment and specialized operating personel and materials which are not easily found in small hospital centers or field laboratories, mainly in developing countries. Moreover, the occurence of losses during the extraction steps lead to lower drug concentrations, and consequently to wrong results.

Thus, it remains a need for methods of monitoring patient compliance whithout the above mentioned disadvantages of the known methods but having sensitivity and specificity sufficient to detect trace amounts of substances contained in complex body fluids. Such monitoring methods would help physicians both in prescribing adequate doses of medication and in monitoring patients to insure that they are ingesting the prescribed amounts. Accordingly, it is to the provision of such improved methods that the present invention is directed.

SUMMARY OF THE INVENTION

The object of the invention is to provide the monitoring or either drug levels in a clinical setting and in public health services and patient compliance with medication prescriptions. The drug levels monitoring is, accomplished by quantitative assays which allow drug detection in body fluids down to 0.3 $\mu$g/ml. The method based on extraction of the drug from biological fluids is characterized by a prior deproteinizing step in conditions that at least 97% of the drug is recovered, i.e. by carrying out the deproteinizaing step in the presence of $ZnSO_4$ it is possible to efficiently strip off the drug which became bound to proteins contained in the biological fluid. Noteworthy the method of the invention is specially useful for a drug assay from blood which contains much more protein than other biological fluids such as urine, saliva, tear fluid.

One embodiment of the present invention is a method for drug level detection by using a simplified and effective deproteinizing step from body fluids, such as plasma, blood, urine, saliva, tear fluid, followed by drug extraction and measurement using an accurate technique, such as a colorimetric assay or a High-Performance Liquid Chromatography method.

In a particular embodiment, the invention is directed to a method to quantify rifampicin in order to monitor its levels in body fluids and also to a kit of tuberculosis diagnosis based oh rifampicin concentration measurement.

DETAILED DESCRIPTION OF THE INVENTION

Figure 1A:
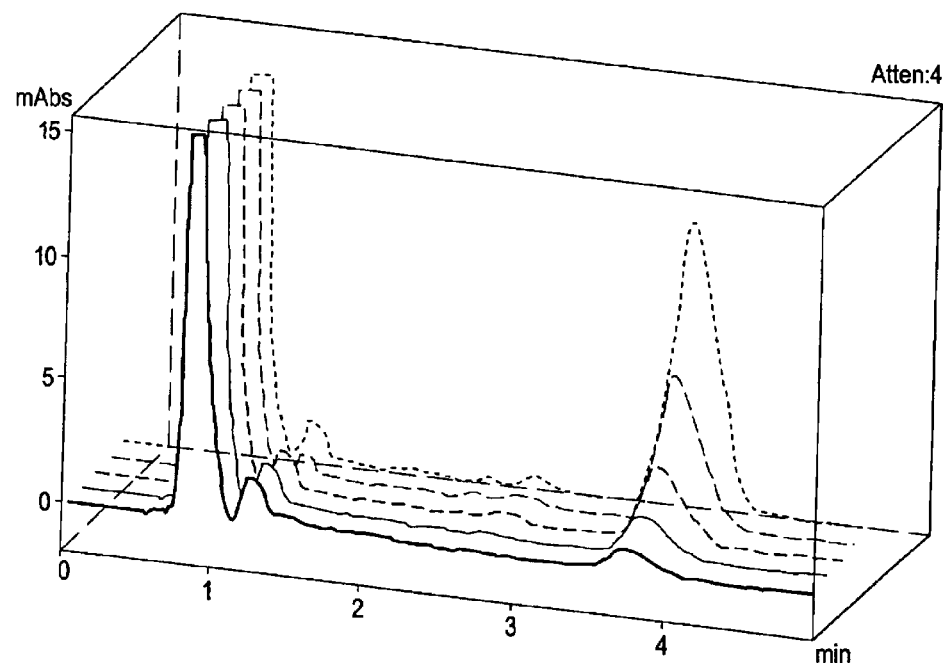
FIG. 1 shows the reproducibility and accuracy of the method of the present invention illustrated by HPLC chromatograms of synthetic mixtures of rifampicin with body fluids: (A) rifampicin in plasma at 25; 12.5; 6.25; 3.13 and 1.56 $\mu$g/ml; (B) various samples of rifampicin synthetic mixture in saliva at a concentration of 2.0 $\mu$g/ml; (C) various samples of rifampicin synthetic mixture in urine at a concentration of 18 $\mu$g/ml.

In medication maintenance programs, the patient is initially prescribed by a medication and dose based on several factors. These ordinarily include the severity and duration of illness, amounts and types of medications previously used, previous medical history, patient sex, pregnancy status, patient weight and ingestion of other therapeutic medications. In certain instances, the pathogenic agent may develop a significant level of resistance to the drug or therapeutic combinations and therefore a loss of sensitivity to the administered drug. In this respect, the regular intake of drugs is of great importance.

To determine compliance with the prescribed medication dose, random body fluid samples, e.g. urine or blood are obtained from the patient and parent drug and/or its metabolites concentration is measured. Consistently, antifungal drugs concentrations in blood are measured either to ensure adequate concentrations of the drug and to avoid unwanted side-effects caused by undue concentration (Anon: British Society for Antimicrobial Chemotherapy Working Party: Laboratory monitoring of antifungal chemotherapy. *The Lancet*. Vol. 337. pp. 1577–1580. 1991).

Paticularly in the treatment of tuberculosis, the regular intake of drugs is of great importance. Indeed, to reach the goal of elimination of tuberculosis as a public health problem, it is important to provide control programmes with an efficient tool to follow up the treatment. This can be accomplished by methods developed to detect even minor amounts of the drug or its metabolites in the body fluids. Such tests should also be carried out in chemotherapeutic studies for assessment of the efficacy of new drugs or regimens, particularly if the drugs are not taken under direct supervision.

Although rifampicin, isoniazid, pyrazinamide and ethambutol are the most commonly, used drugs for the treatment of tuberculosis, rifampicin and isoniazid are considered the first-line choice antituberculosis agent. The rifampicins are antibiotics produced by the bacterium *Streptomyces mediterranei* and is an amphoteric substance which is soluble both in organic solvents and in acid pH water. Rifampicin is metabolized by the liver, especially during its first passage through the hepatoportal system, and its principal metabolite is 25-desacetylrifampicin. The pharmacokinetics of rifampicin varies with the age of the patient and is affected by impaired liver and kidney function. In such circumstances, therapeutic drug monitoring of rifampicin might be of value in optimizing the dose. It is excreted from the human body unaltered and as its metabolites, desacetyl-rifampicin being its principal metabolite. Most of the drug is eilminated in the bile (about 80%) and some by the kidneys.

Almost all known methods of determining rifampicin concentration in body fluids, e.g. Microbiological, HPLC and colorimetric methods, need a number of prior extraction steps to separate rifampicin and its metabolites from the complex mixture. Such step plays an important role in the acuracy of the assay because it is necessary to strip off rifampicin and its metabolites which became bound to body fluid proteins. But, in these methods, the removing treatment of the interferent components demands time and results in losses of the analytes, i.e. rifampicin and particularly its metabolites which are present in very low concentrations.

According to the present invention just one extraction step is used as prior treatment before drug level detection. Aqueous zinc sulfate, an appropriate solvent and the body fluid to be analyzed are mechanically mixed, and after centrifuging, the deproteinized supernatant phase is carefully recovered to determine drugs and its metabolites concentrations.

The prior separation of proteins from the body fluid to permit interferents elimination before drug level analysis is known. Accordingly, Frijus-Plessen described a deproteinizing step in an assay to determine the concentration of the anti-retroviral drugs ddI, ddC and AZT (see Frijus-Plessen N., Michaelis H. C., Foth H. e Kahl G. F. (1990). "Determination of 3'-azido-3'-deoxythymidine, 2',3'-dideoxycytidine, 3'-fluoro-3'-deoxythymidine and 2',3'-dideoxyinosine in biological samples by high-performance liquid chromatography". Chrombio. Elsevier Science Publishers B. V. Amsterdam. 534: 101–107). The proteins contained in blood are precipitated by using a saturated ammonium sulfate solution. In fact, the salting out of proteins is a well-known and frequently used method in protein purification. Scopes, R. K. (Scopes, R. K. *Protein Purification Principles and Practice*. Second Edition. Springer-Verlag. New York. Chapter 3. Pp 50. 1988) mention that the most effective salts used as salting out agents are those with multiple-charged anions such as sulfate, phosphate and citrate. In addition, it is cited that the cation is relatively less important, and even so monovalent ions should be used, with $NH_4^+ > K^+ > Na^+$ in precipitation effectiveness.

Despite these assertions we have now found that the separation of proteins from complex mixtures, such as blood or plasma, is not effective unless zinc sulfate is used. Indeed, the separation of the interferent proteins by precipitating them from the drug containing body fluid is not obtained when saturated ammonium sulfate solution is used in the deproteinizing step. Moreover, according to the invention, a relative low concentration of zinc sulfate is advantageouly used. The concentration of the zinc sulfate solution may vary from 0.1M to 5M, and preferably from 0.2M to 1.0M.

Thus, the complete method for monitoring patient compliance and drugs bioavailability of the present invention comprises the following steps: (1) mixing and shaking mechanically the body fluid with aqueous zinc sulfate solution, an appropriate solvent and, optionally an anti-oxidizing agent to precipitate proteins and strip off bound drug; (2) centrifugating the mixture to obtain the separation of phases; (3) recovering the supernatant which, is used for the drug concentration measurement using an accurate technique, such as a colorimetric assay or a High-Performance Liquid Chromatography method.

The solvent used in the deproteinizing step are known and depends on the solubility properties of the drug is being measured. In the case of rifampicin and its metabolites, despite acetonitrile/2-propanol (1:1) is preferred, several organic solvents can be used, such as benzene, toluene, dichloromethane, chloroform or its mixtures. For antimonials, itraconazole and proteinase or the reverse transcriptase inhibitors, such as 2',3'-dideoxyinosine (ddI), 2',3'-dideoxycytidine (ddC) or 3'-azido-2,3'-dideoxythymidine (AZT), polar solvents, in particular water, are used.

The anti-oxidizing agents used in the deproteinizing step are also known to those skilled in the art aiming to slow down the occurrence of oxidation reactions. Ascorbic acid may be cited as an example.

Drug concentration is measured by a suitable technique. Colorimetric and HPLC methods are preferred and well known (e.g., see McConnell, J. B., Smith, H., Davis, M., Williams, R. "Plasma rifampicin assay for an improved solvent extraction technique. Br J. Cin Pharmac. 8: 506–507. 1979; Acocella, G., Nonis, A., Gialdroni-Grassi, G., Grassi, C. "Comparative bioavailability of isoniazid, rifampicin, and pyrazinamide administered in free combination and in a fixed triple formulation designed for daily use in antituberculosis chemotherapy". Am Rev Respir Dis. 138: 882–5. 1988.; Ishii, M. Agata, H. "Determination of rifampicin and its main metabolites in human plasma". J Chromatogr. 426: 412–6. 1988; Vanakoski, J., Mattila, M. J., Vainio, P., Idänpään-Heikkila, J. J. and Tornwall. "150 mg fluconazole does not substantially increase the effects of 10 mg midazolam or the plasma midazolam concentrations in healthy subjects". Int J Clin Pharmacol The. 33(9): 518–523. 1995; (see Frijus-Plessen N., Michaelis H. C., Foth H. e Kahl G. F. (1990). "Determination of 3'-azido-3'-deoxythymidine, 2',3'-dideoxycytidine, 3'-fluoro-3'-deoxythymidine and 2',3'-dideoxyinosine in biological samples by high-performance liquid chromatography". Chrombio. Elsevier Science Publishers B. V. Amsterdam. 534: 101–107).

Figure 1B:
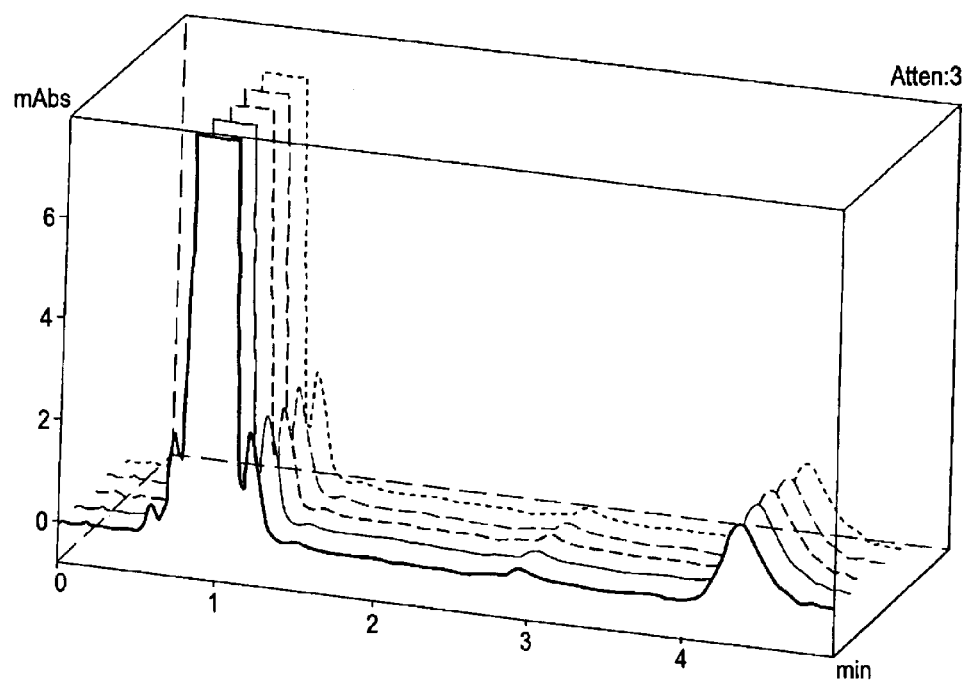
Figure 1C:
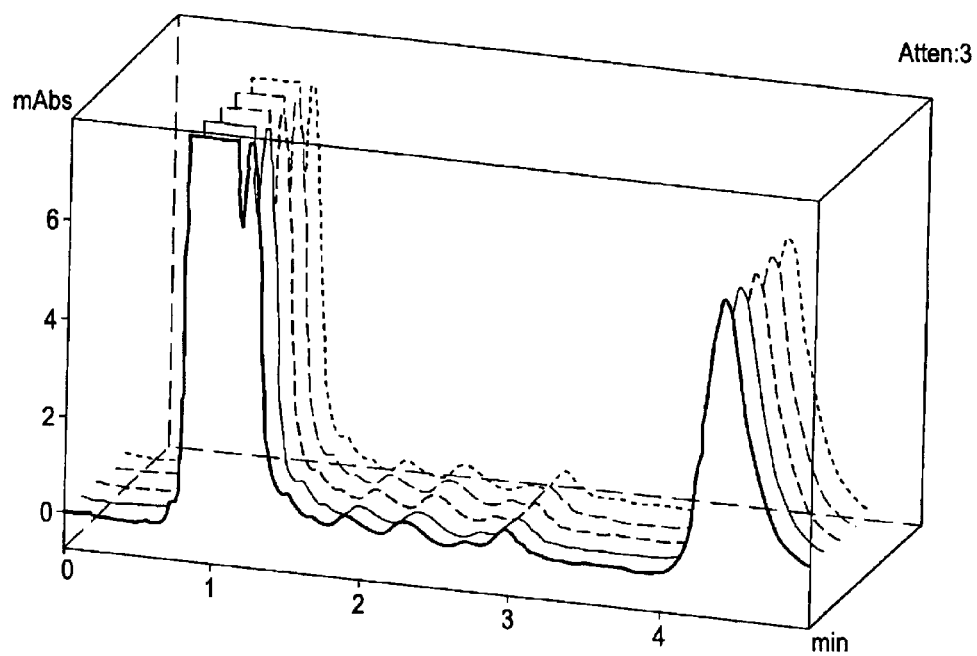

In the case of rifampicin and its metabolites, colorimetry is the most preferred when simplicity combined with accuracy is required. The rifampicin concentration is determined by spectrophotometric measurement of the supernatant organic phase at 340 nm. But the HPLC method may also be used, and antioxidant substances can be added to the mixture of aqueous zinc sulphate, organic solvent and the body fluid to retard oxidation. Assay conditions, in this case, are also easily found in the related art, e.g. Frijus-Plessen et al. FIG. 1 demonstrates the reproducibility and accuracy of the method of the present invention through HPLC chromatograms.

Figure 2:
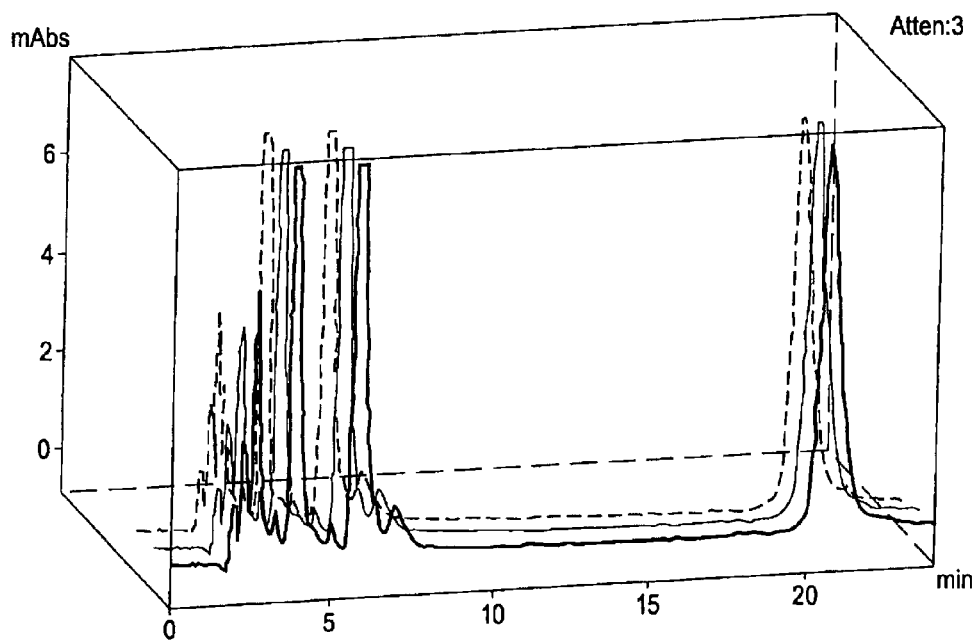
FIG. 2 shows the reproducibility and accuracy of the method of the present invention illustrated by a HPLC chromatogram of a synthetic mixture of 2',3'-dideoxycytidine (ddC), 2',3'-dideoxyinosine (ddI) and 3'-azido-2,3'-dideoxythymidine (AZT) with plasma at a concentration of 20 µg/ml.
Figure 3:
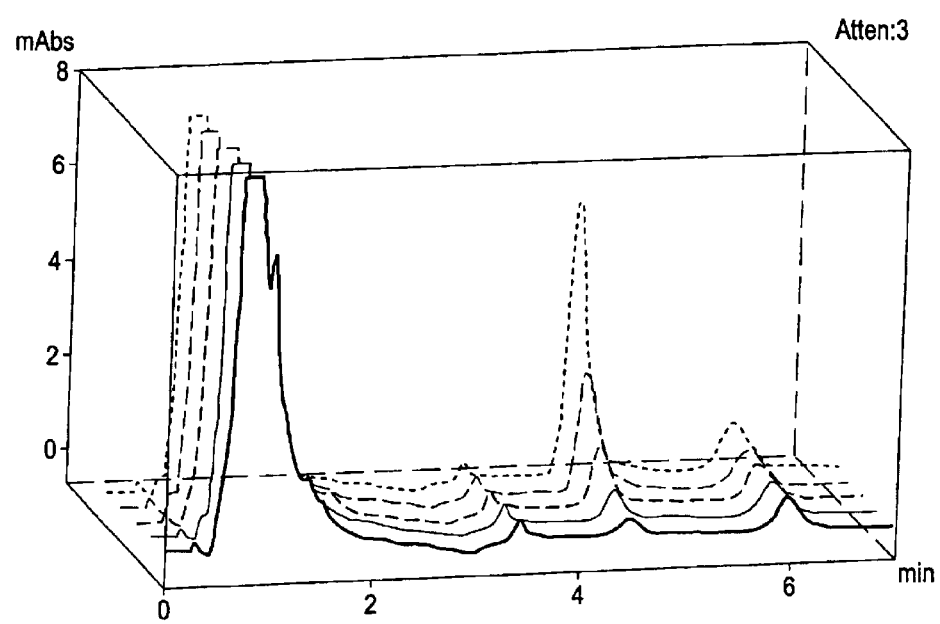
FIG. 3 shows the reproducibility and accuracy of the method of the present invention illustrated by a HPLC chromatogram of a synthetic mixture or itraconazole with plasma at concentrations of 20; 10; 5; 2.5; and 1.25 µg/ml.

FIGS. 2 and 3 show the reproducibility and accuracy of the method of the present invention illustrated by HPLC chromatograms of synthetic mixtures or rifampicin, 2',3'-dideoxycytidine (ddC), 2',3'-dideoxyinosine (ddI), 3'-azido,-2,3'-dideoxythymidine (AZT) and itraconazole with body fluids.

To perform the rifampicin level detection method of the present invention, a kit containing standard solutions of aqueous zinc sulphate, organic solvent and body fluid, e.g. plasma standards, serum standards containing a known amount of rifampicin are provided. Procedure instructions may also be supplied. A typical kit of the invention consists of a solution of aqueous $ZnSO_4$ in a concentration from 0.1M to 5M, an organic solvent selected from the group of acetonitrile/2-propanol (1:1), benzene, toluene, dichloromethane, chloroform or its mixtures and a set of mixtures of plasma with rifampicin at several concentrations to obtain the standard curve for the user conditions. Particularly preferred are aqueous ZnSO in a concentration of 0.2M to 1.0M and a mixture of $CH_3CN/CH_2CHOHCH_3$ (1:1) as the solvent.

Figure 4A:
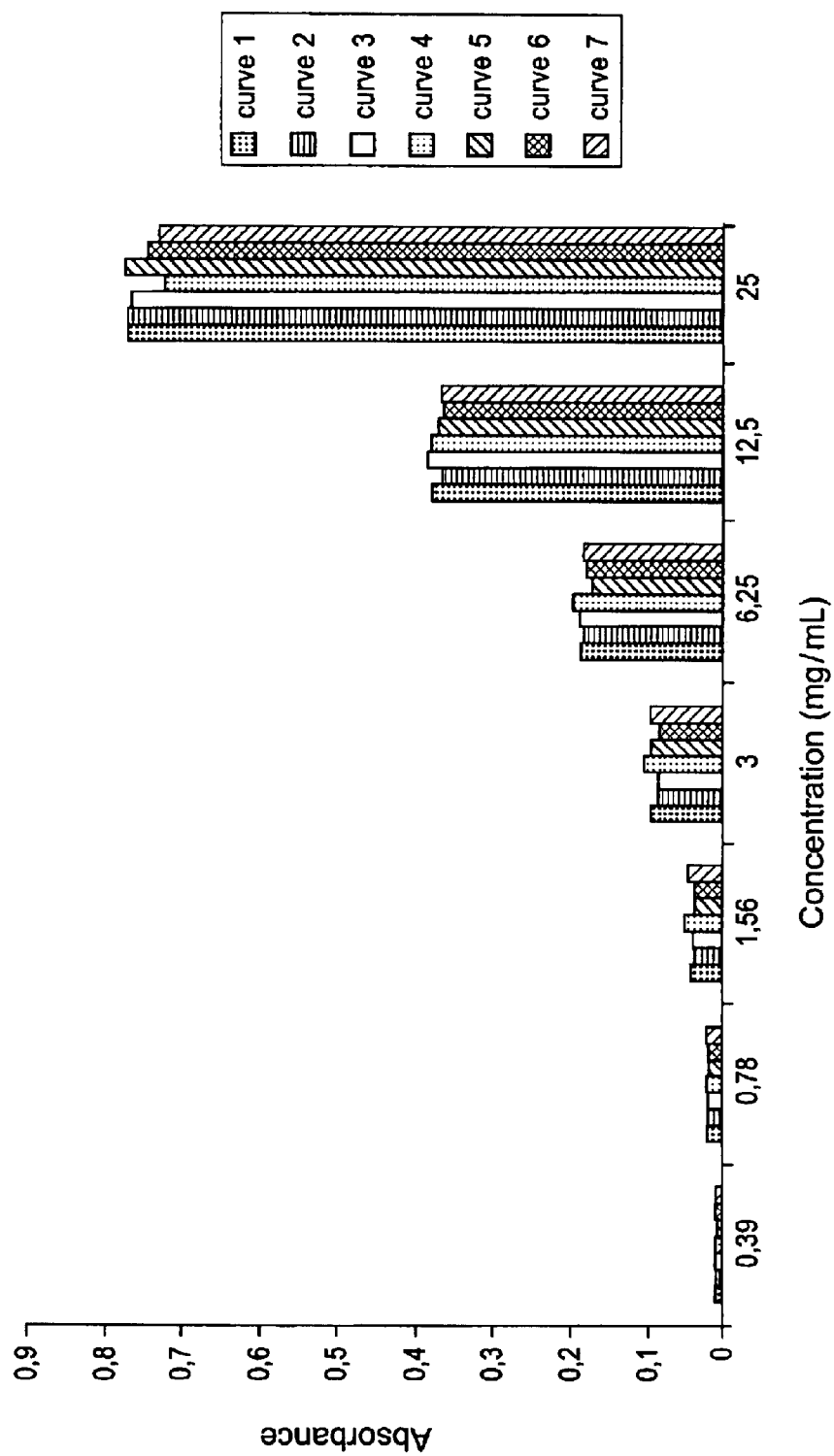
FIGS. 4A and 4B illustrate a set of standard curves demonstrating that Beer's law-is followed for the range of 0.39 to 25 µg/ml of rifampicin in plasma, and the reproducibility of the method of the present invention by colorimetric measurements at 340 nm.
Figure 4B:
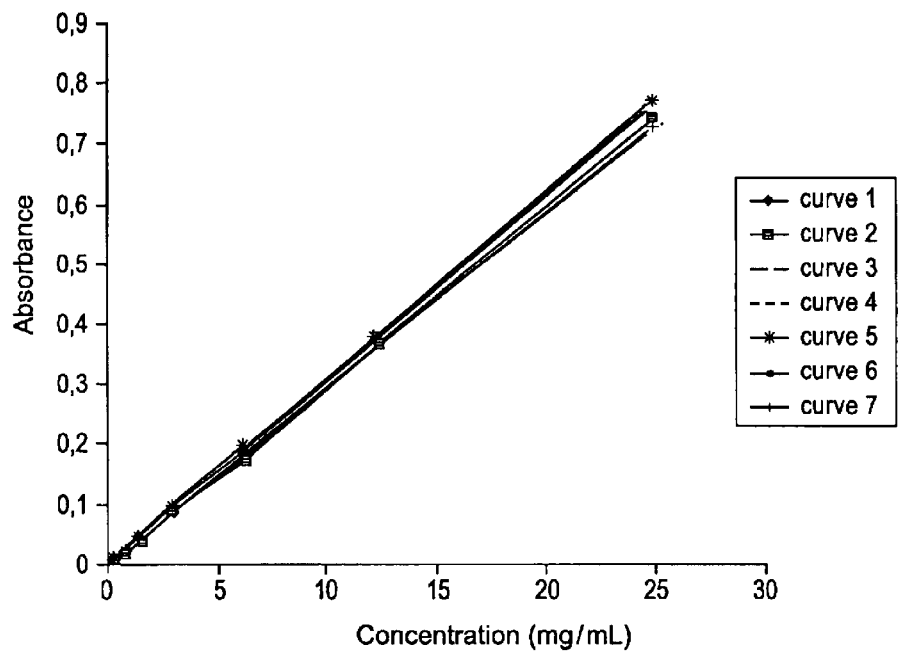

FIGS. 4A and 4B and Table 1 refer to the standard curves of the colorimetric assay for mixtures of rifampicin and plasma at several concentrations ranging from 0.39 to 25 $\mu$g/ml and $\lambda$=340 nm. These standard curves for plasma extract had correlation coefficients of 0.9999 and the mean recoveries of rifampicin were at least 98%, corroborating the efficacy of the one step prior treatment of the present invention.

Figure 5:
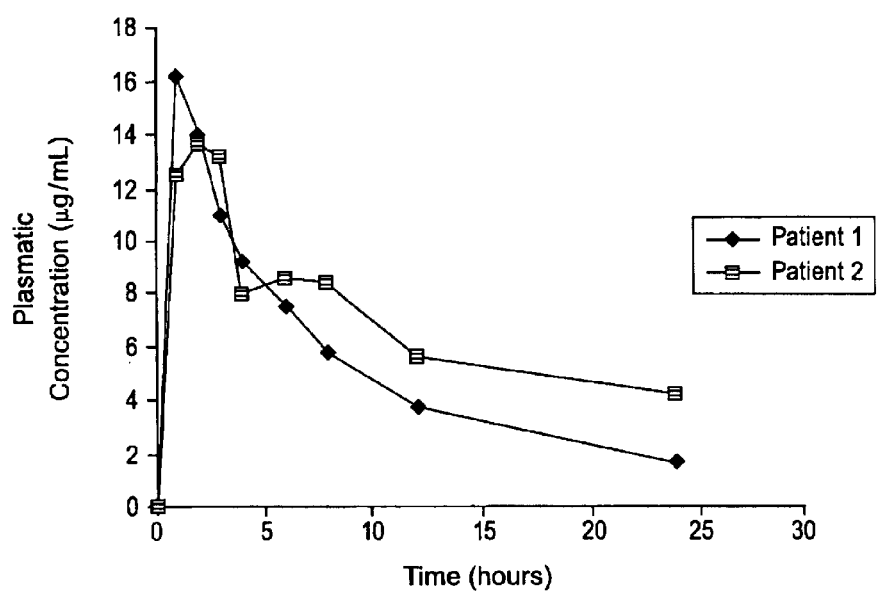
FIG. 5 illustrates the usefulness of the method of the present invention in rifampicin pharmacokinetics studies, showing the variation of rifampicin plasma concentration at the indicated time intervals for two HIV positive patients with tuberculosis.

The method is also suitable for pharmacokinetics studies of rifampicin and its metabolites. FIG. 5 shows the rifampicin levels in plasma or two HIV positive patients with tuberculosis following oral administration of 600 mg of rifampicin, during a period of 24 hours subsequent to drug administration. The curve corresponding to the sample of one of the patients is irregular because he is suffering from hepatic problems.

TABLE 1

Standard Curves of Rifampicin concentration in plasma

| Concentration ($\mu$g/ml) | Absorbance | | | | | | | Mean | Standard Deviation | Variation Coefficient |
| --- | --- | --- | --- | --- | --- | --- | --- | --- | --- | --- |
| | Curve 1 | Curve 2 | Curve 3 | Curve 4 | Curve 5 | Curve 6 | Curve 7 | | | |
| 0.39 | 0.013 | 0.012 | 0.014 | 0.012 | 0.009 | 0.008 | 0.011 | 0.01128571 | 0.00213809 | 0.00668153 |
| 0.78 | 0.022 | 0.021 | 0.019 | 0.021 | 0.020 | 0.019 | 0.021 | 0.02042857 | 0.00113389 | 5.55052723 |
| 1.56 | 0.042 | 0.040 | 0.042 | 0.046 | 0.040 | 0.043 | 0.043 | 0.04228571 | 0.00205866 | 4.86846088 |
| 3.00 | 0.096 | 0.088 | 0.088 | 0.094 | 0.090 | 0.087 | 0.097 | 0.09142857 | 0.00415761 | 4.54738507 |
| 6.25 | 0.189 | 0.180 | 0.191 | 0.191 | 0.178 | 0.181 | 0.185 | 0.18500000 | 0.00544671 | 2.9441684 |
| 12.50 | 0.382 | 0.368 | 0.370 | 0.365 | 0.375 | 0.368 | 0.367 | 0.37071429 | 0.00587975 | 1.58605901 |
| 25.00 | 0.770 | 0.748 | 0.768 | 0.724 | 0.775 | 0.746 | 0.732 | 0.75185714 | 0.0197689 | 2.62934297 |
| Correlation Coefficient | 0.99997559 | 0.99998962 | 0.99983102 | 0.99991144 | 0.99986669 | 0.99998607 | 0.99994411 | | | |

The advantages of the method of the present invention as compared with available methods described in literature are: accurate determination of the drug concentration in body fluid; faster determination of a selected drug level in a body fluid; simpler technique which is useful in smaller hospital centers and field laboratories; and lower costs permitting its use in public health systems.

The following examples are illustrative of the invention and represent preferred embodiments. Those skilled in the art may know, or be able to find using no more than routine experimentation, to employ other appropriate materials and techniques, such as the above mentioned extracting substances and measuring methods.

EXAMPLE 1

This example is to illustrate the determination of rifampicin level in plasma using a colorimetric assay.

500 µl of plasma is mixed with 200 µl of 0.5M $ZnSO_4$, 500 µl of acetonitrile:2-propanol (1:1, v/v) and ascorbic acid 0.5 mg/ml in a vortex mixer and centrifuged for 3 minutes at 3,500 rpm. The spectophotometric measurement of the supernatant organic phase permit the determination of rifampicin level in plasma.

This assay lasts 15 minutes. it is a very fast procedure as compared with other assays comprising many steps for rifampicin separation and does not require expensive equipment and specialized operating personel which are necessary in more sophisticated techniques, such as HPLC.

EXAMPLE 2

The purpose of this example is to illustrate the determination of rifampicin level in plasma using a HPLC procedure.

To 500 µl of plasma, urine or saliva containing unknown amount or rifampicin are added 250 µl of $ZnSO_4 \cdot 7H_2O$ 0.5M, 1 ml of acetonitrile:2-propanol (1:1, v/v) and 0.5 mg/ml of ascorbic acid. The mixture is mechanically shaken for 5 minutes and, then centrifuged for 10 minutes at 3,500 rpm. A 20 µl aliquot of the supernatant organic phase is injected into chromatographic column.

The chromatographic operating conditions are: the mobile phase consisting of 38% of B in A, where A=0.1M $KH_2PO_4$ (10% $H_2O$) and B=$CH_3CN$, pH=3.5. The mixture is pumped at a constant flow-rate or about 2 ml/minute under a pressure of about 40 bar at room temperature, such as 30° C.; the column is a RP 18 10 µm 250×4.6 mm column; and the detection was carried out at 254 nm.

Calibration samples were prepared by measuring 20 µl of rifampicin solution. Three to six samples containing 1.25 to 20 µg/ml of rifampicin were prepared. The calibration graphs (peak area against time) were straight lines. The complete calibration was repeated every day. Retention time for rifampicin was 4 minutes as showed in FIG. 1.

What is claimed is:

1. Method of monitoring patient compliance and bioavailability of drugs contained in a body fluid consisting essentially of the following steps:
   (a) mixing and shaking mechanically the body fluid with a 0.1 M to 5.0 M aqueous zinc sulfate solution to precipitate proteins, and an appropriate solvent to extract the drug during deproteinizing, in a single step, and recovering at least 97% of the drug;
   (b) centrifuging the mixture of (a), to obtain the separation of phases;
   (c) recovering the supernatant of (b) and measuring the drug concentration in body fluid using a colorimetric assay or a High-Performance Liquid Chromatography method, and
   (d) obtaining drug levels down to at least 0.3 µg/ml.

2. Method according to claim 1 wherein the concentration of the aqueous zinc sulfate solution ranges from 0.2 M to 1.0 M.

3. Method according to claim 1 or 2 wherein the appropriate solvent is a polar solvent or a non polar solvent or mixtures thereof.

4. Method according to claim 3 wherein the solvent is an organic solvent selected from the group consisting of acetonitrile/2-propanol, benzene, toluene, dichloromethane, chloroform and mixtures thereof.

5. Method according to claim 3 wherein the solvent is selected from the group consisting of water, an alcohol and a mixture thereof.

6. Method according to claim 1 wherein, optionally, an antioxidizing agent is included in step (a).

7. Method according to claim 1 or 2 or 6 wherein the drug is rifampicin.

8. Method according to claim 4 wherein the drug is rifampicin.

9. Method according to claim 1 wherein the drug is selected from the group consisting of an antimonial, an itraconazole, a proteinase and a reverse transcriptase inhibitor.

10. Method of monitoring patient compliance and bioavailability of rifampicin contained in a small amount of a body fluid comprising the following steps:
    (a) mixing and shaking mechanically the body fluid with a 0.1 M to 5.0 M aqueous zinc sulfate solution, an organic solvent selected from the group consisting of acetonitrile/2-propanol, benzene, toluene, dichloromethane, chloroform and a mixture thereof, to extract rifampicin and, optionally, an antioxidizing agent to precipitate proteins and strip off bound drug at same time or in a single step;
    (b) centrifuging the mixture of (a) to obtain the separation of phases;
    (c) recovering the organic phase supernatant of (b) and measuring the drug concentration in said supernatant by using a colorimetric assay or a High-Performance Liquid Chromatography method down to at least 0.3 µg/ml.

11. Method according to claim 10 wherein the concentration of the aqueous zinc sulfate solution ranges from 0.2 M to 1.0 M.

12. Method according to claim 10 or 11 wherein the solvent used in step (a) is acetonitrile/2-propanol.

13. Method according to claim 10 wherein said antioxidizing agent is ascorbic acid.

14. Method according to claim 10 wherein the rifampicin concentration is determined through spectrophotometric measurement at 340 nm.

15. Kit for measuring rifampicin concentration in a body fluid containing the following components:
    (a) a standard solution of 0.1 M to 5.0 M of aqueous zinc sulfate, optionally, including an antioxidizing agent;
    (b) an organic solvent selected from the group consisting of acetonitrile/2-propanol, benzene, toluene, dichloromethane, chloroform and a mixture thereof;
    (c) a serum standard containing a know amount of rifampicin to prepare a standard curve for user conditions.

16. Kit according to claim 15 wherein the concentration of the aqueous zinc sulfate solution ranges from 0.2 M to 1.0 M.

17. Kit according to claim 15 wherein said antioxiding agent is ascorbic acid.

18. Kit according to claim 15 wherein the organic solvent is acetonitrile/2-propanol.

* * * * *